United States Patent [19]

Bryson

[11] 4,130,245
[45] Dec. 19, 1978

[54] LIQUID DISPENSING PACKAGE
[75] Inventor: John D. Bryson, Milwaukee, Wis.
[73] Assignee: Will Ross, Inc., Milwaukee, Wis.
[21] Appl. No.: 837,524
[22] Filed: Sep. 29, 1977
[51] Int. Cl.² ............................................. A61L 9/04
[52] U.S. Cl. ....................................... 239/34; 239/56
[58] Field of Search .................... 239/34, 36, 53–56, 239/542

[56] References Cited
U.S. PATENT DOCUMENTS

| 2,132,554 | 10/1938 | Baldwin | 239/53 |
| 3,623,659 | 11/1971 | Maierson | 239/56 |
| 3,774,850 | 11/1973 | Zeman | 239/542 |
| 3,785,556 | 1/1974 | Watkins | 239/34 X |

Primary Examiner—Robert W. Saifer
Attorney, Agent, or Firm—Michael, Best & Friedrich

[57] ABSTRACT

Disclosed herein is a generally flat envelope or package for controllably dispensing into the atmosphere a liquid substance which is normally liquid and vaporizable under atmospheric temperature and pressure conditions. The package includes two sheets which are made of flexible material permeable to the liquid substance and are peripherally sealed to each other in opposing relation to form a hermetically sealed chamber encapsulating the liquid substance. The interior surfaces of the chamber walls are joined together at a plurality of parallel, transversely spaced locations to divide the chamber into a plurality of smaller elongated chambers having wall portions which, although flexible enough to collapse under atmospheric pressure in response to permeation of the liquid substance therethrough, are sufficiently rigid to minimize outwardly bulging thereof by the liquid substance when the package is in a nonhorizontal position and to encourage surface contact of the entire interior surfaces of the smaller chambers with the liquid substance as it permeates to the surrounding atmosphere.

12 Claims, 3 Drawing Figures

LIQUID DISPENSING PACKAGE

BACKGROUND OF THE INVENTION

This invention relates to devices for controllably dispensing a normally liquid, vaporizable substance to the atmosphere and, more particularly, to packages which encapsulate a liquid substance and are made from a material through which the liquid substance can permeate to the surrounding atmosphere.

Hermetically sealed envelopes or packages containing odorants, deodorants, insecticides, attractants, repellents and the like in concentrated liquid form and made from a flexible plastic material through which the liquid substance can permeate as a liquid and then vaporize into the surrounding atmosphere have been used to dispense such substances. Examples of envelopes or packages of this type are disclosed in the Watkins U.S. Pat. No. 3,785,556, issued Jan. 15, 1974 and the Watkins U.S. Pat. No. 3,885,737, issued May 27, 1975. Attention is also directed to the Poitras U.S. Pat. No. 3,343,664, issued Sept. 26, 1967.

To obtain a uniform dispensing rate of the liquid substance, it is desirable to maintain maximum surface contact between the interior surfaces of the package and the liquid substance throughout the effective life of the package. Prior art packages, such as those disclosed in the aboveidentified patents, usually include a single chamber for the liquid substance and the flexible walls of this chamber collapse under the influence of atmospheric pressure as the liquid substance is dispensed. If such a package is located in a nonhorizontal position during dispensing, the flexible walls of the package tend to be bagged or bulged outwardly by the liquid substance, permitting the liquid substance to accumulate in a lower portion. Consequently, it is possible for a substantial portion of the interior surfaces of the package to be out of contact with the liquid with a resultant reduction in the rate at which the liquid substance is dispensed.

SUMMARY OF THE INVENTION

The invention provides a dispensing envelope or package which contains an encapsulated permeable liquid substance and is arranged to encourage maximum surface contact between the interior surface of the package and the liquid substance throughout the effective life of the package irrespective of the orientation of the package.

More particularly, the invention provides a package for controllably dispensing into the atmosphere a substance which is normally liquid and vaporizable under atmospheric temperatures and pressure conditions. The package includes first and second sheets, at least one of which is made from a flexible material permeable to the liquid substance, and which are peripherally sealed together in opposing relation to form a hermetically sealed chamber having opposed walls. The interior surfaces of the chamber walls are joined together at a plurality of spaced locations to divide the chamber into a plurality of smaller chambers which are filled with the liquid substance. The smaller chamber wall portions formed from the flexible material collapse under atmospheric pressure in response to permeation of the liquid substance therethrough to the surrounding atmosphere and have sufficient rigidity to minimize outwardly bulging thereof by the liquid substances and to encourage surface contact of the entire interior surface of the smaller chamber walls with the liquid substance as it permeates to the surrounding atmosphere.

In one embodiment, the first and second sheets include a film of a thermoplastic material and the liquid substance is an odorant, deodorant, insecticide, attractant, repellent, or the like which is permeable to the thermoplastic material.

In another embodiment, the chamber walls are joined together at parallel, transversely spaced locations and the smaller chambers are elongated and extend in parallel relationship. These joints preferably are formed by heat sealing and are discontinuous so that the liquid substance can flow from one smaller chamber to another.

In a further embodiment, the first and second sheets include an exterior layer of a porous material which does not become sticky at the temperatures used to form the heat seal joints.

One of the principal features of the invention is the provision of a package which is suitable for dispensing a liquid substance through the walls of the package and which is arranged to maximize surface contact between the interior surfaces of the package walls and the liquid substance during use.

Another of the principal features of the invention is the provision of a package which is suitable for dispensing a liquid substance through the walls of the package and includes simple means for rigidifying the package walls so as to minimize outward bulging thereof by the liquid substance when the package is in a nonhorizontal position.

Other features and advantages of the invention will become apparent to those skilled in the art upon reviewing the following detailed description, the drawing and the appended claims.

Figure 1:
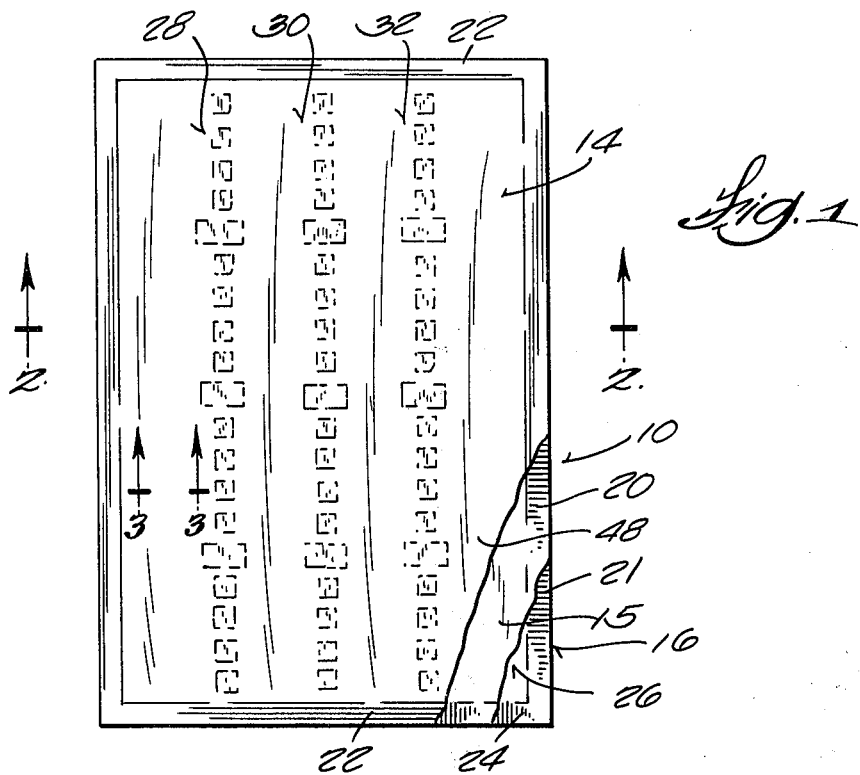
FIG. 1 is a top plan view, partially broken away, of a dispensing package incorporating various of the features of the invention.

Before explaining at least one embodiment of the invention in detail, it is to be understood that the invention is not limited in its application to the details of construction and the arrangements of the components set forth in the following description or illustrated in the drawing. The invention is capable of other embodiments and of being practiced and carried out in various ways. Also, it is to be understood that the phraseology and terminology employed herein is for the purposes of description and should not be regarded as limiting.

DESCRIPTION OF THE PREFERRED EMBODMENTS

Illustrated in the drawing is a generally flat envelope or package 10 for controllably dispensing a concentrated liquid substance 12, such as an odorant, deodorant, insecticide, attractant, repellent or the like, which is normally liquid and vaporizable under atmospheric temperature and pressure conditions.

The package includes two sheets 14 and 16, at least one of which is permeable to the particular liquid substance being dispensed. In the specific construction illustrated, each of the sheets 14 and 16 include a film of a thermoplastic material 15, such as polyethylene or polypropylene, which is permeable to the liquid substance 12.

The sheets 14 and 16 include respective peripheral margins, i.e., opposed side or lateral margins 20 and 21, and opposed end margins 22 and 24, which are sealed to each other in opposing relation to form a hermetically sealed chamber designated generally at 26 in FIG. 1 for containing a quantity of the liquid substance 12 under substantially gas free conditions. That is, the chamber 26 is formed in a manner whereby the interior is substantially free of any gases which could affect the rate of permeation of the liquid substance 12 through the package walls. While various techniques can be used, the package 10 preferably is formed by heat sealing together the peripheral margins of the sheets 14 and 16 in substantially the same manner disclosed in the above-identified Watkins U.S. Pat. No. 3,785,556 which is incorporated herein by reference.

Figure 2:
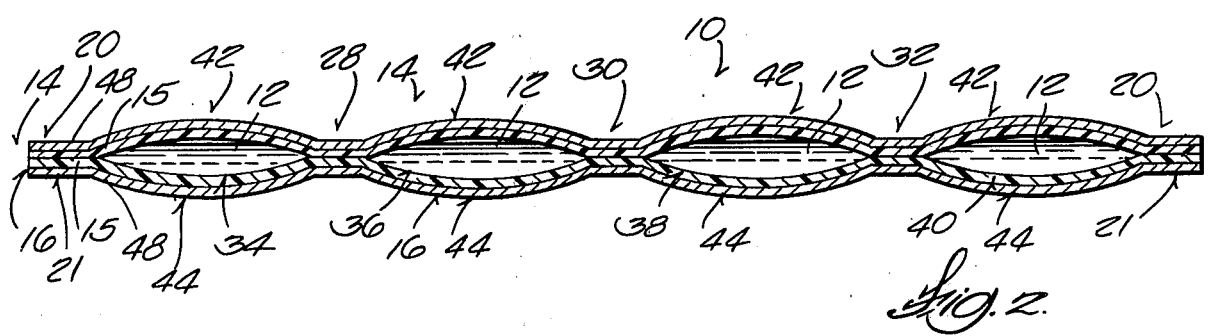
FIG. 2 is an enlarged sectional view taken generally along line 2—2 in FIG. 1.

In order to prevent the walls of the chamber 26 from being bagged or bulged outwardly by the liquid substance 12 when the package 10 is in a nonhorizontal position, the interior surfaces of the portions of the sheets 14 and 16 defining the chamber 26 are joined together at transversely spaced joints 28, 30 and 32 which, as best shown in FIG. 2, divide the chamber 26 into a plurality of smaller chambers 34, 36, 38 and 40, each having opposed wall portions 42 and 44 formed from the respective sheets 14 and 16. The wall portions 42 and 44 of the smaller chambers, while flexible enough to collapse under the influence of atmospheric pressure as the liquid substance 12 permeates therethrough to the surrounding atmosphere, are sufficiently rigid to minimize bagging or outward bulging thereof by the encapsulated liquid substance 12.

While the small chambers 34, 36, 38 and 40 can have various configurations and the joints 28, 30 and 32 delimiting these chambers can be formed by various suitable techniques, in the specific construction illustrated, these joints are formed by heat sealing the interior surfaces of the sheets 14 and 16 together and extend in parallel relationship to each other and the lateral margins of the package. The resulting small chambers 34, 36, 38 and 40 are elongated and extend in parallel relationship. Such an arrangement facilitates gravity filling of the small chambers 34, 36, 38 and 40 with the liquid substance 12 and subsequent sealing of one of the end margins of the sheets 14 and 16 to complete the assembly.

Figure 3:
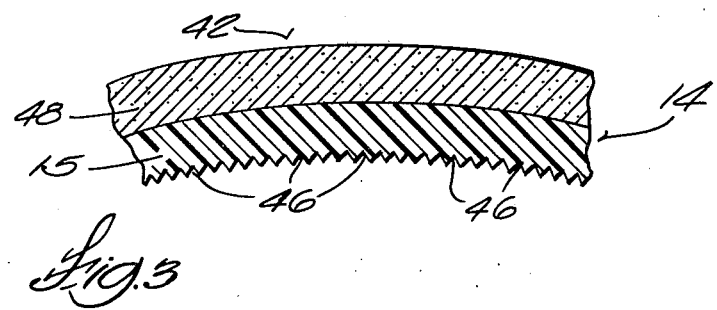
FIG. 3 is an enlarged, fragmentary, sectional view taken generally along line 3—3 in FIG. 1.

For example, when the package 10 is fabricated by a method similar to that disclosed in the Watkins U.S. Pat. No. 3,785,556, a tubular package, having sealed lateral side and lower margins similar to the package 11 illustrated in FIG. 1 of the patent, is formed first. The joints 28, 30 and 32 can then be formed, preferably after the side walls of the tubular package defining the chamber 26 have been bowed outwardly as illustrated in FIG. 3 of the Watkins U.S. Pat. No. 3,785,556, by moving opposed heat sealing heads including transversely spaced ribs or ridges (not shown) into clamping engagement with the exterior surfaces of the sides of the tubular package. The interior surfaces of the tubular package, i.e., the interior surface of the thermoplastic films, are heat sealed together at the joints 28, 30 and 32 corresponding to the locations of the ribs or ridges on the heating heads. The resulting elongated small chambers 34, 36, 38 and 40 are subsequently filled to overflowing with the liquid substance 12 at atmospheric pressure. The upper margin of the lower filled package and the lower margin of the superadjacent package are simultaneously heat sealed closed as illustrated in FIGS. 5 and 6 of the Watkins U.S. Pat. No. 3,785,556 and the filled, sealed lower package is severed from the tubular package, as illustrated in FIG. 7 of that patent, to complete the assembly.

As alluded to above, the small chambers 34, 36 38 and 40 can be formed in various shapes other than that illustrated. For example, the small chambers can have a bubble-like shape with a circular, rectangular, polygonal, etc., cross section, in which case the joints delimiting the smaller chambers can be formed after the chamber 26 has been filled with the liquid substance 12.

In order to encourage uniform distribution of the liquid substance 12 throughout the interior of the package 10 as the liquid substance is dispensed, the joints 28, 30 and 32 preferably are discontinuous. That is, the interior surfaces of the sheets 14 and 16 are tacked together at intermittent or spaced locations along each of the joints 28, 30 and 32 as illustrated in FIG. 1. This permits the liquid substance 12 to flow from one small chamber to another as the walls 42 and 44 of the small chambers 34, 36, 38 and 40 collapse in response to permeation of the liquid substance therethrough to the surrounding atmosphere. Also, the interior surfaces of the sheets 14 and 16 preferably are embossed, scored or otherwise textured to provide a plurality of recesses 46 as shown in FIG. 3. The recesses 46 serve as capillary channels for evenly distributing the liquid substance 12 over the interior surfaces of the small chamber walls 42 and 44 when they reach a fully or nearly fully collapsed position as described in the Watkins U.S. Pat. No. 3,785,556.

When the joints 28, 30 and 32 are formed by heat sealing as described above, the heating heads used for forming these joints tend to stick to the outer surfaces of the thermoplastic film 15. In accordance with one embodiment of the invention, this problem is obviated by covering the tubular package, prior to heat sealing, with a porous barrier material 48, such as a porous paper material, which does not become sticky upon being heated to the temperatures required for forming the heat seal joints 28, 30 and 32. During heat sealing of the peripheral margins of the package 10 and heat sealing to form the joints 28, 30 and 32, the barrier material 48 is fused to the thermoplastic films 15 at the locations of the heat seals and forms the exterior surface of the resultant package 10. Accordingly, the barrier material 48 must be sufficiently porous so as not to inhibit the permeation of the liquid substance 12 through the package walls.

Various of the features of the invention are set forth in the following claims.

What is claimed is:

1. A package for controllably dispensing into the atmosphere a substance which is normally liquid and vaporizable under atmospheric temperature and pressure conditions, said package comprising
    first and second sheets peripherally sealed together in opposing relation to form a hermetically sealed chamber having opposed side walls formed from said first and second sheets, at least one of said sheets being made of a flexible material which is permeable to the liquid substance, and
    means joining the interior surfaces of said chamber walls together at a plurality of spaced locations to divide said chamber into a plurality of smaller chambers which are filled with the liquid substance under atmospheric pressure and have wall portions formed from said chamber walls, said wall portions formed from said flexible material collapsing under atmospheric pressure in response to permeation of the liquid substance therethrough to the surrounding atmosphere and having sufficient rigidity to minimize outward bulging thereof by the liquid substance and to encourage surface contact of the entire interior surface of said wall portions with the liquid substance as the liquid substance permeates to the surrounding atmosphere.

2. A package according to claim 1 wherein said first and second sheets include a film of a flexible thermoplastic material and the liquid substance is an odorant, deodorant, insecticide, attractant or repellent which is permeable to said thermoplastic material.

3. A package according to claim 2 wherein said thermoplastic material is polyethylene.

4. A package according to claim 2 wherein said means joining said chamber walls comprises a discontinuous heat seal joint.

5. A package according to claim 3 wherein said first and second sheets include an exterior layer of a porous material which does not become sticky at the temperatures used to form said heat seal joint.

6. A package according to claim 1 wherein said joining means joins said chamber walls together at parallel, transversely spaced locations and said smaller chambers are elongated and extend in parallel relation.

7. A package according to claim 1 wherein said joining means provides a discontinuous joint which permits the flow of the liquid substance between said smaller chambers.

8. A package according to claim 1 wherein the interior surfaces of said wall portions include a plurality of recesses to provide a plurality of capillary channels.

9. A generally flat package for controllably dispensing into the atmosphere a substance which is normally liquid and vaporizable under atmospheric temperature and pressure conditions, said package comprising first and second sheets of a flexible thermoplastic material which is permeable to the liquid substance and peripherally heat sealed to each other in opposing relation to form a hermetically sealed chamber having opposed walls formed from said first and second sheets, the interior surfaces of said chamber walls being joined together by a plurality of parallel, transversely spaced, discontinuous heat seal joints to divide said chamber into a plurality of smaller elongated chambers which are filled with the liquid substance under atmospheric pressure and extend in parallel relation, and said smaller chambers having wall portions which are formed from said chamber walls and collapse under atmospheric pressure in response to permeation of the liquid substance therethrough to the surrounding atmosphere and have sufficient rigidity to minimize outward bulging thereof by the liquid substance and to encourage surface contact area between the entire interior surfaces of said wall portions and the liquid substance as the liquid substance permeates to the surrounding atmosphere.

10. A package according to claim 9 wherein the liquid substance is an odorant, deodorant, insecticide, attractant or repellent which is permeable to said thermoplastic material.

11. A package according to claim 10 wherein
said first and second sheets include an exterior layer of a porous material which does not become sticky at the temperatures used to form said heat seal joints.

12. A package according to claim 11 wherein the interior surfaces of said wall portions include a plurality of recesses to provide a plurality of capillary channels.

* * * * *